United States Patent [19]

Ida et al.

[11] Patent Number: 4,770,774
[45] Date of Patent: Sep. 13, 1988

[54] COLUMN FOR REMOVING $\beta_2$-MICROGLOBULIN

[75] Inventors: Nobuo Ida; Hiroshi Kataoka; Tetsunosuke Kunitomo, all of Kamakura, Japan

[73] Assignee: Toray Industries, Inc., Tokyo, Japan

[21] Appl. No.: 57,968

[22] PCT Filed: Sep. 18, 1986

[86] PCT No.: PCT/JP86/00485
§ 371 Date: May 14, 1987
§ 102(e) Date: May 14, 1987

[87] PCT Pub. No.: WO87/01597
PCT Pub. Date: Mar. 26, 1987

[30] Foreign Application Priority Data

Sep. 19, 1985 [JP] Japan .................... 60-207250

[51] Int. Cl.⁴ .................................. B01D 13/00
[52] U.S. Cl. ............................ 210/259; 210/317; 210/321.72; 422/44; 436/518
[58] Field of Search ............... 422/44, 45, 70; 210/317, 646, 321.72, 638, 632, 259; 436/518, 529, 530, 531, 807

[56] References Cited

U.S. PATENT DOCUMENTS

| | | | |
|---|---|---|---|
| 3,669,878 | 6/1972 | Marantz | 210/646 |
| 4,257,884 | 3/1981 | Lim | 210/632 |
| 4,321,192 | 3/1982 | Jain | 210/646 |
| 4,329,152 | 5/1982 | Lauwerys | 436/534 |
| 4,569,919 | 2/1986 | Toth | 436/531 |

FOREIGN PATENT DOCUMENTS

| | | | |
|---|---|---|---|
| 54-37821 | 3/1979 | Japan | 436/531 |
| 56-93046 | 7/1981 | Japan | 436/531 |
| 2030294 | 4/1980 | United Kingdom | 436/531 |

OTHER PUBLICATIONS

Termin, FEBS Letters, vol. 61, No. 1, (Jan. 1976), pp. 59–62, North-Holland Pub. Co.-Amsterdam.
Sevier, Clin. Chem., vol. 27, No. 11, (1981), 1797–1802.

Primary Examiner—Kenneth M. Schor
Attorney, Agent, or Firm—Austin R. Miller

[57] ABSTRACT

A column comprising an insoluble carrier and an anti-$\beta_2$-microglobulin antibody immobilized to the carrier can specifically adsorb and remove $\beta_2$-microglobulin in the blood. This column is useful for the prevention and treatment of diseases such as carpal tunnel syndrome observed in patients undergoing blood dialysis.

2 Claims, 4 Drawing Sheets

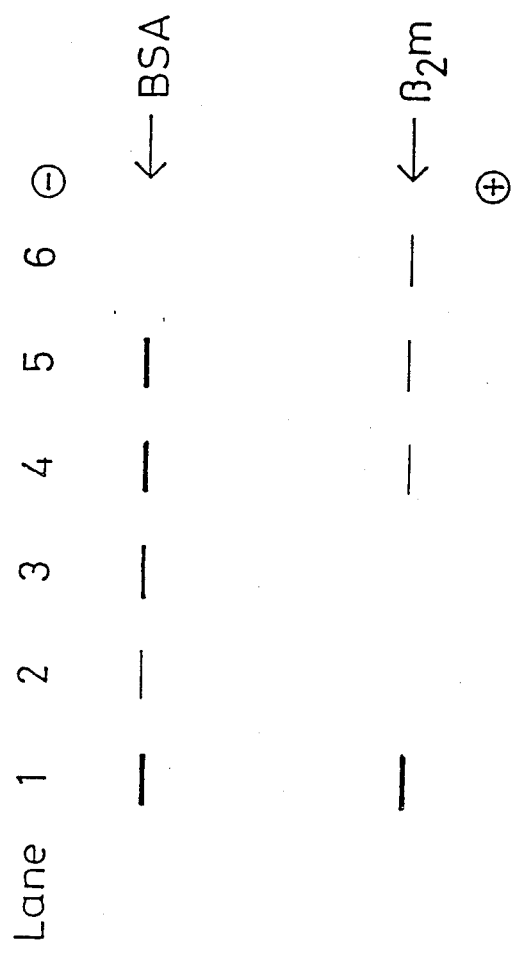

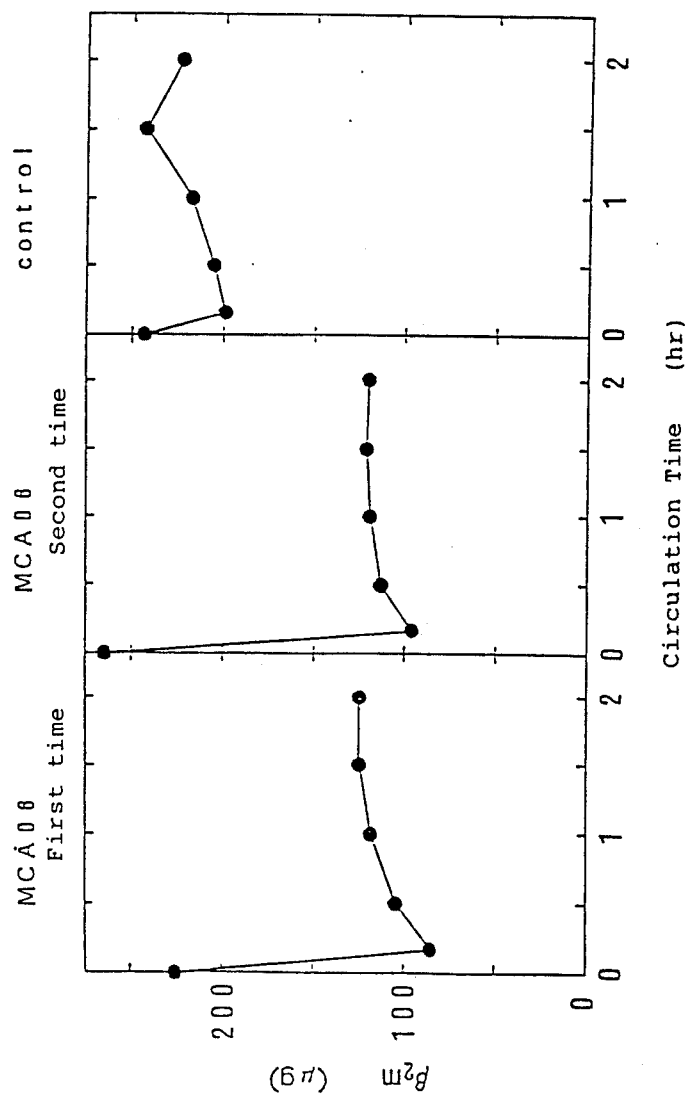

COLUMN FOR REMOVING $\beta_2$-MICROGLOBULIN

TECHNICAL FIELD

This invention relates to a column for removing $\beta_2$-microglobulin. More particularly, this invention relates to a column which specifically adsorbs and removes $\beta_2$-microglobulin in the blood.

BACKGROUND ART $\beta_2$-microglobulin is a light chain of a double-stranded protein constituting the major histocompatibility antigen (in case of human, it is HLA, class I), and occurs on the surfaces of most of cells. It also occurs in the body fluid in the free form, but the physiological function of the free $\beta_2$-microglobulin has not yet been known. The full amino acid sequence thereof has been determined for human and other various animals, and its three dimensional structure has been determined by X-ray analysis for bovine. It has been proved that it is a simple protein with a molecular weight of about 12,000, which does not have a sugar chain, and that it has structurally high homology with the C domain (constant domain) of immunogulobulin. Further, the homology of the amino acid sequence thereof between different species is 60 to 80%, and thus it is considerably high (Proc. Natl. Acad. Sci. 257, 2619 (1982)).

The $\beta_2$-microglobulin level in the blood of the patients suffering from nephropathy, who are undergoing artificial blood dialysis for a long period, is as high as 10 to 100 times that of normal human. It is assumed that this is because that $\beta_2$-microglobulin which is decomposed in the kidney is not removed by the blood dialysis and thus accumulates in the blood.

The present inventors separated and analyzed the amyloid proteins deposited on the diseased part of a patient suffering from carpal tunnel syndrome to find that most of the amyloid proteins are $\beta_2$-microglobulin. Thus, it is assumed that carpal tunnel syndrome is caused by the deposition of the $\beta_2$-microglobulin on the diseased part, which is accumulated in the blood with high level. Thus, it is expected that carpal tunnel syndrome can be prevented by removing the $\beta_2$-microglobulin in the blood along with the artificial blood dialysis. Further, it is possible that $\beta_2$-microglobulin is involved in the deposition of amyloid on the parts other than the carpal tunnel.

Heretofore, no disease has been known of which cause is clarified to be the $\beta_2$-microglobulin in the blood, and so how to remove the $\beta_2$-microglobulin in the blood has not been considered at all.

DISCLOSURE OF THE INVENTION

The object of the present invention is to provide a method for selectively removing $\beta_2$-microglobulin in the blood.

The object can be accomplished by the present invention which provides a column for adsorbing and removing $\beta_2$-microglobulin, which employs immobilized anti-$\beta_2$-microglobulin antibody.

BRIEF DESCRIPTION OF THE DRAWINGS

FIGS. 1(a) and 1(b) show examples of circuits which employs blood dialyzer and $\beta_2$-microglobulin-removing column together, wherein FIG. 1(a) shows an example in which they are connected in series, and FIG. 1(b) shows an example in which they are connected in parallel;

FIG. 2 is a schematic view showing the results of SDS-polyacrylamide gel electrophoresis of column fractions obtained in Example 1;

FIGS. 4(a), 4(b) and 4(c) show the change in time of the amount of the remaining $\beta_2$-microglobulin in the blood, wherein 4(a) shows the results obtained by using a column in which anti-$\beta_2$-microglobulin antibody is immobilized, 4(b) shows the results obtained by reusing the column of (a), and 4(c) shows the results obtained by using a column in which anti-$\beta_2$-microglobulin is not immobilized.

BEST MODE FOR CARRYING OUT THE INVENTION

Figure 1A:
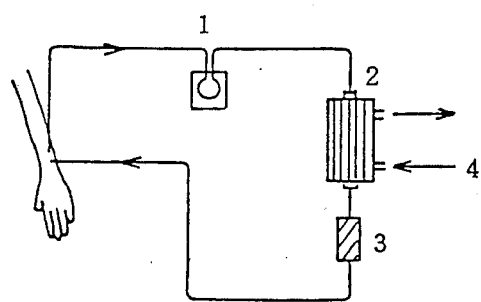

Both of a polyclonal antibody which is obtained by immunizing animals such as mice, rats, rabbits, goats and sheep, and a monoclonal antibody obtained by using a cell hybridization technique can be used as the anti-$\beta_2$-microglobulin antibody in the present invention. $\beta_2$-microglobulin to be immunized may be derived from any animal if the obtained antibody can bind the human $\beta_2$-microglobulin. However, for the promotion of the binding efficiency, $\beta_2$-microglobulin derived from human or monkey, especially human is preferred. A peptide fragment thereof or a synthetic peptide, which has the same immunogenic ability, may also be used. In order to effectively remove $\beta_2$-microglobulin and not to affect the function of the blood cells, it is preferred to use a monoclonal antibody which does not bind to the $\beta_2$-microglobulin constituting the HLA on the cell surfaces, and which binds to the free $\beta_2$-microglobulin alone.

The insoluble carrier used in the present invention includes agarose, cellulose, dextran, polyacrylamide and polystyrene derivatives. The material of the insoluble carrier is preferably a hydrophilic material to which only a small amount of blood components are non-specifically adsorbed. The carrier may be in the form of beads, fibers or films. In cases where the beads are used, the diameter of the beads is not limited as long as the $\beta_2$-microglobulin-containing fluid can circulate. However, to reduce the flow resistance, those having a diameter of 50 to 3,000 $\mu$m, especially 200 to 3,000 $\mu$m are preferably used. Further, it is preferred to use beads which are physically strong and of which diameters are not changed so much by a pressure applied thereto.

The binding of the antibody to the insoluble carrier may be conducted by chemically forming covalent bonds therebetween by using a coupling agent such as cyanogen bromide and carbodiimide, or using a cross-linking agent such as glutaraldehyde. It is also possible to promote the adsorbing ability per an amount of antibody by binding the $\beta_2$-microglobulin via protein A which is preliminary immobilized to the insoluble carrier. In this case, however, it is necessary to chemically cross-link the protein A and the antibody to prevent the escape of the antibody.

The amount of the antibody to be immobilized in the column, and the size of the column are not restricted. To obtain a better curing effect, it is preferred that one column can adsorb not less than 50 mg of $\beta_2$-microglobulin. Since 1 g of the antibody can adsorb 50 mg to 150 mg of antigen $\beta_2$-microglobulin, it is necessary that one column have 300 mg or more of the antibody. It should be noted, however, if 2 or more column is used in a treatment, the amount of the antibody per column can be reduced.

In the treatment, the column for removing $\beta_2$-microglobulin may be used alone. However, in view of the fact that the major subject patients are those undergoing artificial blood dialysis, it is preferred to connect the column in series or in parallel with a blood dialyzer to simultaneously conduct blood circulation in view of the convenience of the operation.

Figure 1B:
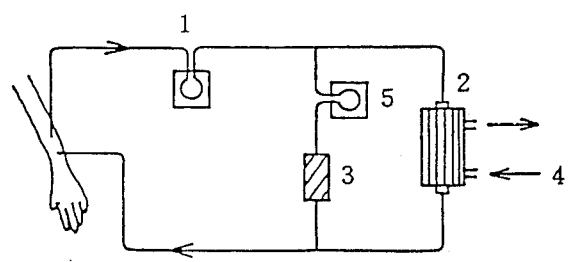

An example in which the column of the present invention is connected to the blood dialyzer will now be described referring to FIG. 1. An example in which the column is connected in series to the blood dialyzer is shown in FIG. 1 (a). The blood taken out of the body of a patient enters a blood dialyzer 2 through a blood pump 1, and then dialyzed with a dialyzing fluid 4. The blood is then subjected to a treatment to remove $\beta_2$-microglobulin in a $\beta_2$-microglobulin-removing column 3, and then returns to the body of the patient. Although the $\beta_2$-microglobulin-removing column 3 is connected after the blood dialyzer 2 as shown in FIG. 1 (a), the column may also be connected before the blood dialyzer 2. An example in which the column and the blood dialyzer are connected in parallel will now be described referring to FIG. 1 (b). The blood taken out of the body of a patient is divided into two directions after passing through the blood pump 1. The blood flow proceeding to one direction enters the blood dialyzer 2 in which the blood is dialyzed with the dialyzing fluid 4. The blood flow proceeding to another direction enters the $\beta_2$-microglobulin-removing column 3 in which the $\beta_2$-microglobulin is removed, after being controlled of its flow rate by an auxiliary pump 5, and gets together with the blood flow from the blood dialyzer 2 and returns to the body. In cases where the column is connected in parallel to the blood dialyzer, the $\beta_2$-microglobulin-removing column may be connected in any portion of the circuit. In cases of connecting the column and the blood dialyzer in parallel, to make the flow rate in the bypass constant, the auxiliary pump 5 may be used as shown in FIG. 1 (b). The control of the flow rate may also be accomplished by appropriately selecting the inner diameters of the tubes of the circuit without using the auxiliary pump 5. The material consitituting the dialysis membrane of the blood dialyzer is not restricted and includes cellulose, cellulose acetate, polymethylmethacrylate, polyacrylonitrile, polysulphones, polyamides, polyesters, polyvinylalcohols and polyvinylalcohol copolymers. To increase the amount of the $\beta_2$-microglobulin removed, it is preferred that the dialysis membrane have a permeability of 2% or more for the proteins with a molecular weight of 10,000.

Whole blood can be passed through the column for removing $\beta_2$-microglobulin of the present invention. Although the operation is complicated, the same effect may be obtained by circulating the plasma from which the blood cells have been removed by a conventional plasma separator, instead of circulating the whole blood.

The column used for adsorption may be regenerated and reused by passing an acidic solution with a pH of about 2 through the used column.

Since the column of the present invention selectively adsorbs $\beta_2$-microglobulin, the $\beta_2$-microglobulin in the blood can be conveniently and effectively removed. Further, the column of the present invention has an advantage that it can be repeatedly used by eluting the adsorbed $\beta_2$-microglobulin.

The present invention will now be described more specifically referring to the examples thereof.

EXAMPLE 1

To 1 ml of an agarose gel ("Affigel 10", manufactured by Bio Rad Laboratories) in which N-hydroxysuccinimide ester groups were introduced via a spacer of 10 atoms length ($-OCH_2CONH(CH_2)NHCO(CH_2)_2-$), 1.46 mg of a commercially available anti-human $\beta_2$-microglobulin monoclonal antibody in 1 ml of 0.1M HEPES-NaOH buffer (pH7.5) was added and the mixture was gently stirred overnight.

To the mixture, 0.1 ml of 1M ethanolamine-HCl (pH8.0) was added and the mixture was allowed to react for 1.5 hours. After blocking the non-reacted N-hydroxysuccinimide ester groups, the gel was washed alternately three times with 1 ml of 0.1M acetic acid-NaOH (pH4.0) and 1 ml of 0.1M carbonic acid-NaOH (pH9.0), each containing 0.5M NaCl. Finally the gel was equilibrated with PBS. The amount of the remaining protein after the immobilization was 0.02 mg, and so 1.44 mg of antibody was immobilized in 1 g of the gel.

In a commercially available small column (0.8 mm of diameter), 0.3 ml of the thus obtained antibody-immobilized gel was packed, and a model solution containing 0.1 mg/ml of bovine serum albumin (BSA) and 0.1 mg/ml of human $\beta_2$-microglobulin in PBS was passed through the column at a flow rate of 2.4 ml/h at room temperature. Upon starting the flow, fractions of 0.63 ml each were recovered by using a fraction collector, and 20 $\mu$l aliquotes of each fraction (2-5) were analyzed by SDS-polyacrylamide electrophoresis.

The results are shown in FIG. 2. FIG. 2 is a schematic view showing the results of the analysis by the electrophoresis. Lane 1 shows the result obtained by subjecting the model protein solution to the electrophoresis before passing through the column, and lanes 2-5 show the results of the electrophoresis of the fractions 2-5, respectively.

The arrow indicates the migrated position of $\beta_2$-microglobulin ($\beta_2$ m) and the reference sample of BSA.

In all of the analyzed fractions 2-5, the amount ratio of the $\beta_2$-microglobulin to the BSA is smaller than in the solution before being subjected to the column, which shows that only $\beta_2$-microglobulin was selectively adsorbed to the column.

Further, after the proteins remained in the column was eluted with PBS, the antigen bound to the antibody was eluted with 50 mM glycine-HCl buffer (pH2.4), and only $\beta_2$-microglobulin was eluted. The result obtained by subjecting the eluted solution to the electrophoresis is shown in FIG. 2, lane 6.

EXAMPLE 2

Through a column prepared in the same manner as in Example 1, a serum containing a high level of $\beta_2$-microglobulin from a patient who was undergoing artificial blood dialysis was passed. From the beginning of the passage, fractions of 0.32 ml each were recovered using a fraction collector.

Figure 3:
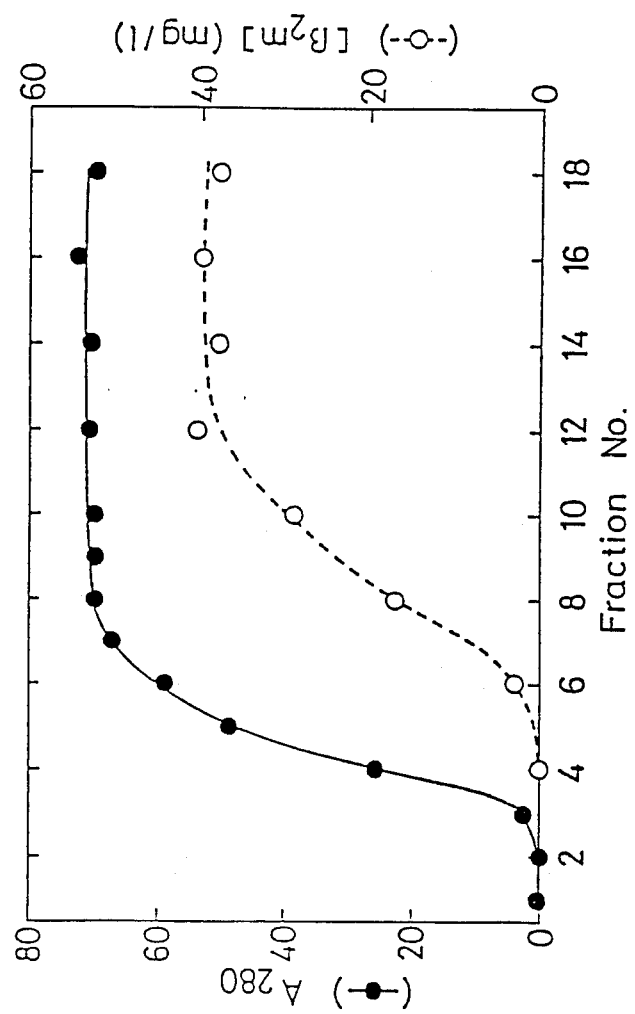
FIG. 3 shows the total amount of proteins and the level of $\beta_2$-microglobulin of the column fractions obtained in Example 2.

Total protein amount (expressed in terms of the absorbance at 280 nm) and the level of the $\beta_2$-microglobulin ($\beta_2$ m) determined by an immunoassay, of the each fraction are shown in FIG. 3. In the fractions up to No. 10, the amount ratio of the $\beta_2$-microglobulin to the total protein amount is significantly smaller than that of the serum before being subjected to the column, which shows that the $\beta_2$-microglobulin was adsorbed and removed by the antibody (As for the serum before being subjected to the column, the absorbance at 280 nm was 72.1, and the $\beta_2$-microglobulin level was 40.5 mg/ml).

It can be seen from the results shown in FIG. 3 that the total amount of the $\beta_2$-microglobulin adsorbed to the column was 0.049 mg, and so 0.11 mg of $\beta_2$-microglobulin was adsorbed per 1 mg of immobilized antibody.

EXAMPLE 3

Two milligrams of the commercially available anti-human $\beta_2$-microglobulin used in Examples 1 and 2 was mixed with 2.8 ml of cellulose beads ("Formyl-Cellulofine", manufactured by Chisso Corporation) in which formyl groups had been introduced via a spacer of 9 atoms length ($-OCH_2CH(OH)CH_2NH(CH_2)_4-$) in 6 ml of potassium phosphate buffer (pH7.0). After reacting for 2 hours at 4° C., dimethylamineborane was added and the reaction was allowed to continue overnight under the reducing condition to prepare beads to which 0.54 mg of antibody was immobilized per 1 ml of carrier. The non-reacted formyl groups were blocked by reacting them with the amino groups of Tris.

In a small column, 2.1 ml (1.1 mg in terms of antibody) of the beads were packed, and 10 ml of normal human blood to which $\beta_2$-microglobulin were added was circulated for 2 hours at a flow rate of 1 ml/min. Small aliquotes of the blood were taken at appropriate times and the $\beta_2$-microglobulin ($\beta_2$ m) levels thereof were determined. The results are shown in FIG. 4 (a). The adsorption was completed within 10 minutes from the commencement of the circulation, and the adsorbed amount was 100 µg, which is about 1/10 of the amount of the antibody used.

After washing the column with 1M glycine-HCl buffer (pH2.8), the same circulation experiment was repeated. As shown in FIG. 4 (b), same or better adsorption than the first circulation was observed. Thus, the column was able to be regenerated. In the control experiment in which cellulose beads having no antibody immobilized thereto were used, the adsorption was scarecely observed (FIG. 4 (c)).

INDUSTRIAL APPLICABILITY

Since the column of the present invention can specifically adsorb and remove the $\beta_2$-microglobulin in the blood as described above, the column of the present invention is very helpful for the prevention and treatment of the complications including amyloidosis such as carpal tunnel syndrome, and osteopathy.

We claim:

1. A system for dialyzing blood comprising a blood dialyzer and a column for removing $\beta_2$-microglobulin including insoluble carrier and an anti $\beta_2$-microglobulin antibody immobilized to the carrier, which column is connected in series or in parallel to the blood dialyzer.

2. The system of claim 1 wherein the antibody is a monoclonal antibody.

* * * * *